US008327519B2

(12) United States Patent
Linares (10) Patent No.: US 8,327,519 B2
(45) Date of Patent: Dec. 11, 2012

(54) MULTI-LEVEL MACHINE FOR DUPLICATING A SECTIONED AND SCANNED BONE END AND FOR PRODUCING A FITTING IMPLANT REPLACEMENT

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 912 days.

(21) Appl. No.: 12/422,412

(22) Filed: Apr. 13, 2009

(65) Prior Publication Data
US 2009/0258101 A1 Oct. 15, 2009

Related U.S. Application Data (60) Provisional application No. 61/044,742, filed on Apr. 14, 2008.

(51) Int. Cl.
*B23C 3/00* (2006.01)
*B23C 1/06* (2006.01)
*B23C 1/20* (2006.01)
*B23Q 11/08* (2006.01)

(52) U.S. Cl. .......... 29/564; 409/113; 409/117; 409/134; 409/137; 409/161; 409/96; 700/163; 700/117; 219/121.67

(58) Field of Classification Search .......... 409/94, 409/96, 113, 93, 98, 104, 107, 109, 111, 409/112, 117, 122, 123, 134, 137, 158, 159, 409/161, 165, 168, 221, 172–173; 700/163, 700/117; 29/564; 219/121.67
See application file for complete search history.

(56) References Cited

U.S. PATENT DOCUMENTS

| | | | | |
|---|---|---|---|---|
| 2,675,652 A | * | 4/1954 | Chiappulini | 409/96 |
| 2,786,500 A | * | 3/1957 | Unterfranz | 144/285 |
| 5,088,864 A | * | 2/1992 | Yanagida | 700/163 |
| 5,231,470 A | | 7/1993 | Koch | |
| 5,274,565 A | | 12/1993 | Reuben | |
| 5,370,692 A | | 12/1994 | Fink et al. | |
| 5,432,703 A | * | 7/1995 | Clynch et al. | 700/163 |
| 5,448,489 A | * | 9/1995 | Reuben | 700/163 |
| 5,449,256 A | * | 9/1995 | Sundman | 409/134 |
| 5,686,992 A | * | 11/1997 | Kawamoto | 356/601 |
| 5,687,467 A | * | 11/1997 | Bergmann et al. | 29/407.05 |
| 5,768,134 A | | 6/1998 | Swaelens et al. | |
| 5,781,652 A | * | 7/1998 | Pratt | 700/163 |
| 5,824,085 A | | 10/1998 | Sahay et al. | |
| 5,926,388 A | * | 7/1999 | Kimbrough et al. | 409/96 |

(Continued)

FOREIGN PATENT DOCUMENTS
EP 917035 A2 * 5/1999
(Continued)

*Primary Examiner* — Erica E Cadugan
(74) *Attorney, Agent, or Firm* — Gifford, Krass, Sprinkle, Anderson & Citkowski, P.C.

(57) ABSTRACT

A machine for producing a three dimensional joint replacement article and which exhibits a three dimensional shaped body incorporating a scanner component for at least receiving a digitized input corresponding to a set of dimensions associated with a replacement article to be produced. Incorporated in die machine is a numerical control guided machining subassembly in communication with at least one material blank corresponding to an article to be produced. Material shavings are vacuum removed and collected for disposal and, following CNC machining, the finished part is deposited into a cavity accessed by a retrieval door for removal.

20 Claims, 10 Drawing Sheets

U.S. PATENT DOCUMENTS

| | | | | |
|---|---|---|---|---|
| 6,144,386 A | * | 11/2000 | Pratt | 715/848 |
| 6,424,877 B1 | * | 7/2002 | Kondo et al. | 700/163 |
| 6,463,351 B1 | | 10/2002 | Clynch | |
| 6,757,582 B2 | | 6/2004 | Brisson et al. | |
| 6,849,223 B2 | | 2/2005 | Dean et al. | |
| 6,944,518 B2 | * | 9/2005 | Roose | 700/117 |
| 6,968,246 B2 | * | 11/2005 | Watson et al. | 700/98 |
| 7,113,841 B2 | | 9/2006 | Abe et al. | |
| 7,203,628 B1 | | 4/2007 | St. Ville | |
| 7,371,067 B2 | | 5/2008 | Anderson et al. | |
| 7,492,476 B1 | | 2/2009 | Dodge et al. | |
| 7,510,558 B2 | | 3/2009 | Tallarida et al. | |
| 2001/0047251 A1 | | 11/2001 | Kemp | |
| 2005/0098915 A1 | | 5/2005 | Long et al. | |
| 2009/0023112 A1 | * | 1/2009 | Ganley et al. | 409/84 |

FOREIGN PATENT DOCUMENTS

JP        01-246051 A   *  10/1989

* cited by examiner

MULTI-LEVEL MACHINE FOR DUPLICATING A SECTIONED AND SCANNED BONE END AND FOR PRODUCING A FITTING IMPLANT REPLACEMENT

CROSS-REFERENCE TO RELATED APPLICATIONS

The present application claims the benefit of U.S. Provisional Patent Application Ser. No. 61/044,742 filed Apr. 14, 2008.

FIELD OF THE INVENTION

The present invention relates generally to the sizing, machining and installation of replacement implants for various living joint applications (for both human and other mammals). More specifically, the present invention teaches a combination portable scanning/sizing and machining device for quickly and effectively producing an artificial joint implant, or a smaller sized artificial replacement associated with a damaged area of an existing joint. A multi-level machining enclosure incorporates scanner, rotatable carousel with varying sized implant blank workpieces, an interior CNC machining compartment, and a lower-most positioned vacuum shaving repository and implant removal station. Additional features include the provision of a remote combination machining laser and digitizing photographic hand tool, this operating within a joint environment and in communication and cooperation with processing capabilities built into the machining enclosure, such as for effectuating replacement of a damaged subset portion of an existing natural or synthetic joint assembly.

BACKGROUND OF THE INVENTION

The prior art is well documented with numerous examples of articles and methods for creating and or producing a three dimensional model of a part, not limited to prosthetic implants. Also known is the use and manipulation of computer numerically controlled (CNC) technology, such being communicated with various turning/cutting machines for performing operations on a workpiece and in order to create a desired three dimensional pattern.

Relevant systems and methods in the medical related technologies include the method of making a perfected medical model on the basis of digitized image information of a body part as taught by Swaelens, U.S. Pat. No. 5,768,134. Image information of the body part is converted by rapid prototyping techniques via a processing unit and a rapid prototype machine into a basic model which, at least in part, perfectly shows positive/negative form associated with at least a portion of the body.

Fink, U.S. Pat. No. 5,370,692 discloses a prosthetic bone implant fabricated to approximately replicate a patient's original bone. Computer aided imaging techniques are applied to generate a data base representing the size and shape of the original bone in a three dimensional coordinate system. The implantable replica is fabricated using the data base and free form manufacturing to sequentially solidify adjoining intervals of fluid material including ceramic particles which may be selectively bonded by sintering or bonding with a polymer and a monomer which is polymerized at selected regions by an incident laser beam.

Abe et al., U.S. Pat. No. 7,113,841, teaches an implant forming method for creating a deficient portion of an existing bone and including generating three dimensional data of the bone based oh a plurality of pieces of tomographic data of the bone. The shape of the missing portion of bone is estimated using three dimensional data corresponding to a symmetrical part of the bone deficient portion.

SUMMARY OF THE INVENTION

The present invention discloses a portable machine for providing the combined features of scanning, digitizing, numerically machining and delivering a three dimensional joint replacement article. The present invention is an improvement over prior NC controlled machining devices in that it provides a compact device which can be utilized and easily operated in many non-traditional locations (such as smaller clinics or hospitals).

The machine exhibits a three dimensional shaped body incorporating a scanner component for at least receiving a digitized input corresponding to a set of dimensions associated with a replacement article to be produced. Incorporated in the machine is a numerical control guided machining subassembly in communication with at least one material blank corresponding to an article to be produced. Material shavings are vacuum removed and collected for disposal and, following CNC machining, the finished part is deposited into a cavity accessed by a retrieval door for removal.

Additional features include a scan window defining access to an interior compartment for receiving an existing article to be measured for replication. A carousel is mounted within the body (such as in an underside facing and accessible location within an upper most compartment which is in communication with the numerical controlled machining subassembly) and supports thereupon a plurality of material blanks corresponding to at least one of implant and cartilage replacement articles. The carousel is then selectively actuated to position a selected blank in communication with the machining subassembly. The carousel further includes adjustable and actuatable mounting assemblies for securing each implant or cartilage blanks in inverted fashion, such as during machining and successive depositing into a drawer associated with said retrieval location.

The retrieval drawer is secured within a finished part repository incorporated into the open interior compartment and separated from the machining subassembly by an inner partition. A waste removal enclosure positioned underneath the machining subassembly incorporates a vacuum interconnected with the machining subassembly, via at least one vacuum port, and in order to remove machined wasted resulting from a numerical controlled operation on the article blank.

A remote hand tool interfaces with the machine and includes a 3D digitizing camera/scanner and at least one of a wired or wireless connection to the scanner component for effectuating digitizing of either a 2D or 3D image associated with the article to be replicated. The hand tool exhibits a stem interconnecting with a handle and exhibiting at least one of a machining laser, portable vacuum communicating to a handle reservoir, and a light emitting source. A power cord communicates with the waste removal enclosure for powering the vacuum, numerical controlled machining subassembly, carousel and scanner. A processor built into the enclosure is communicable with the machining subassembly for dictating a machining protocol associated with an article to be produced.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
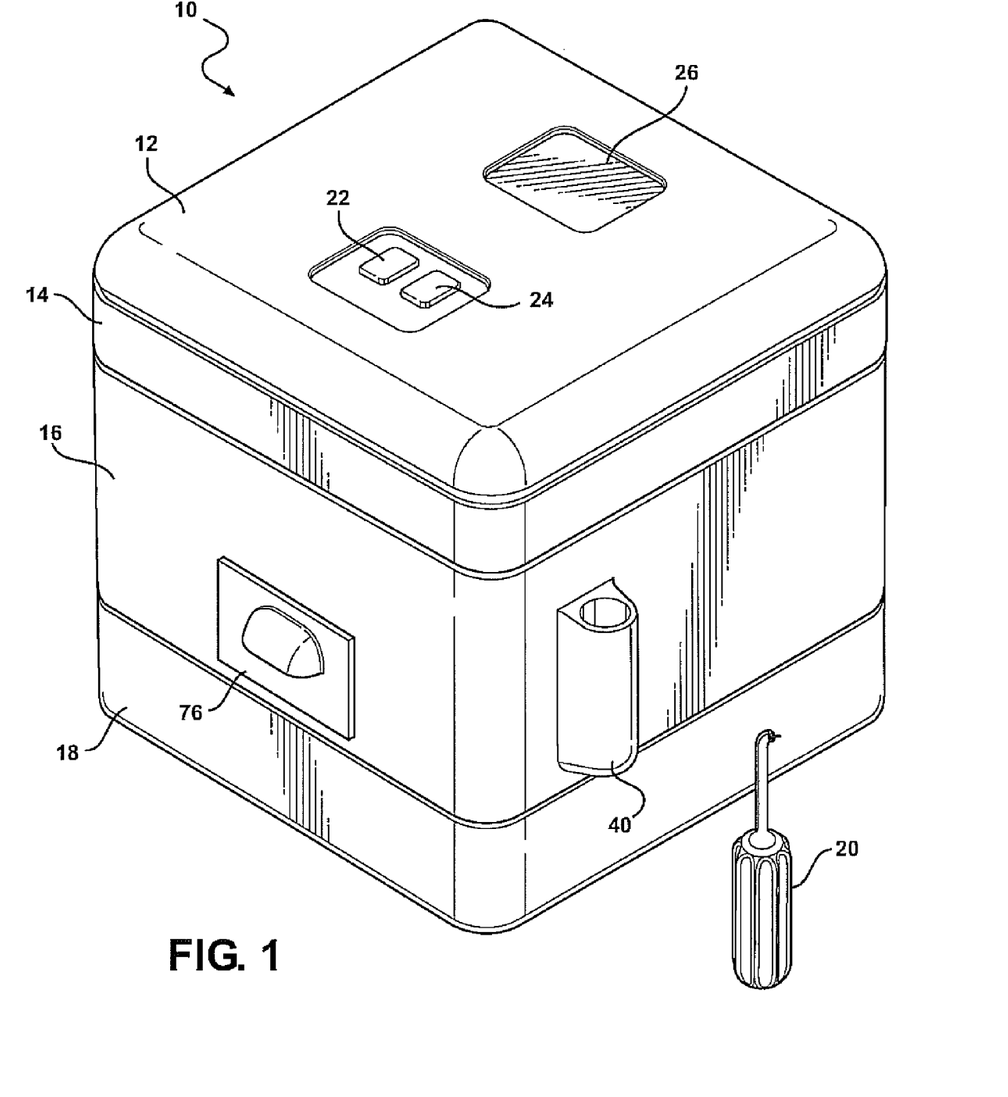
FIG. 1 is a perspective illustration of a portable joint implant manufacturing device according to the present invention.
Figure 2:
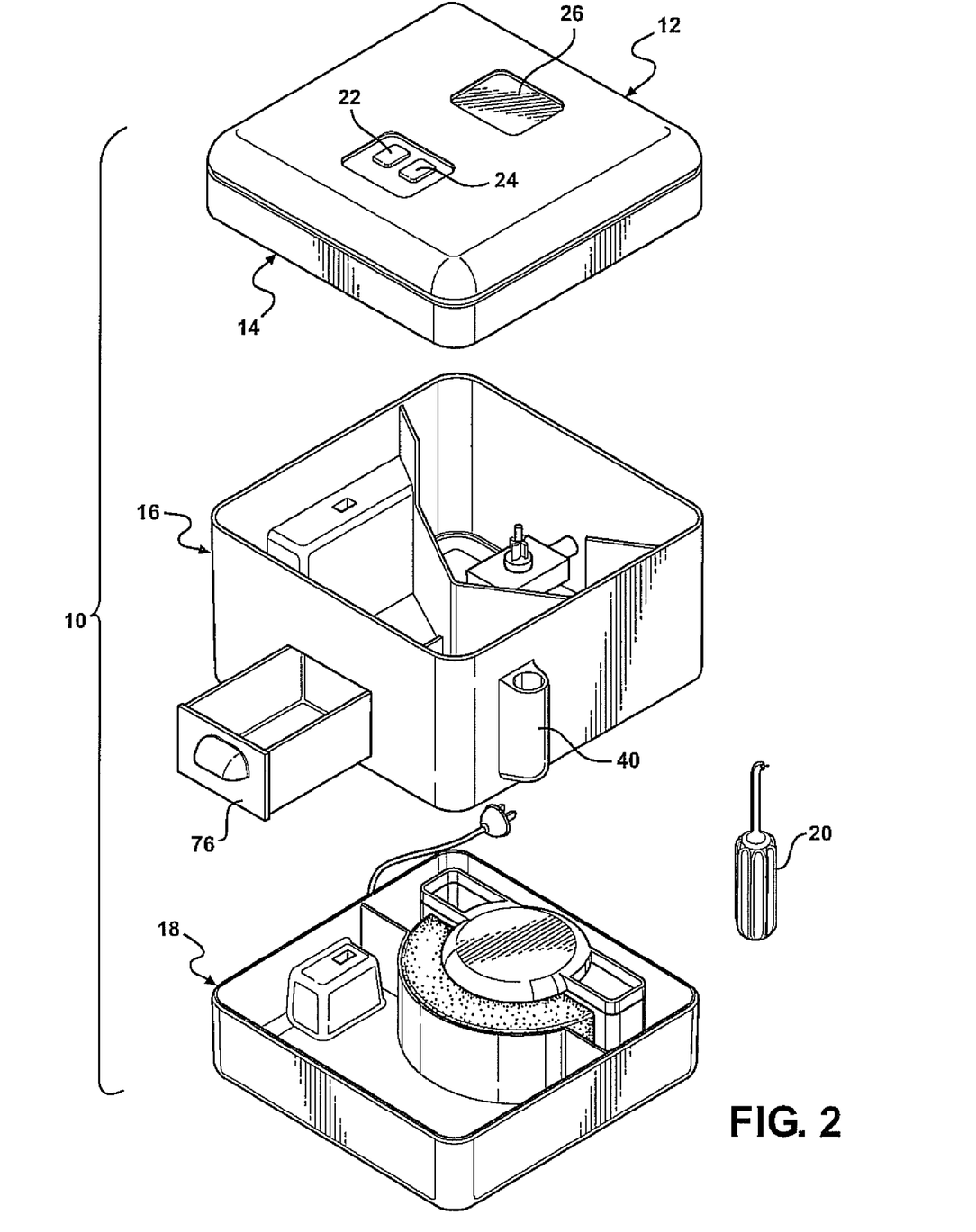
FIG. 2 is an exploded view of the joint implant device.
Figure 3:
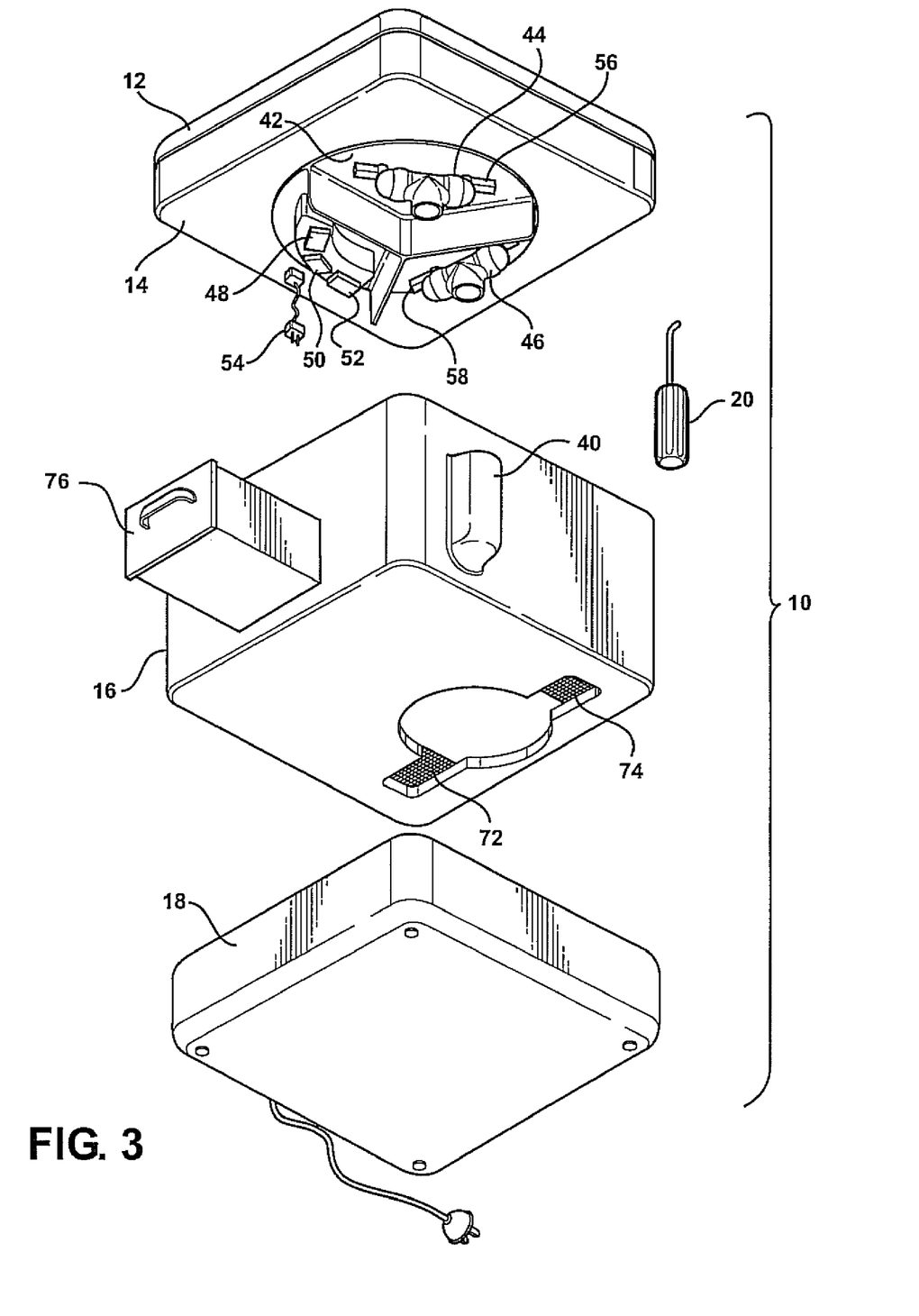
FIG. 3 is a rotated underside and exploded view of the joint implant device in FIG. 2 and better illustrating the feature of the rotatable carousel with multiple implant blanks supported for selective positioning above the CNC compartment mounted machining station.

Referring now to each of FIGS. 1-3, perspective assembled and exploded illustrations are shown at 10 of a portable joint implant manufacturing device according to the present invention. As previously described, the present invention teaches a combination portable scanning/sizing and machining device for quickly and effectively producing an artificial joint implant, or a smaller sized artificial replacement associated with, a damaged area of an existing joint.

A multi-level machining enclosure associated with the implant/cartilage manufacturing device incorporates, in one preferred embodiment, a four level assembly including each of an uppermost scanner compartment 12, a rotatable carousel with varying sized implant blank workpieces 14, an interior CNC machining compartment 16, and a lower-most positioned vacuum shaving repository and implant removal station 18. Additional features include the provision of a remote combination machining laser and digitizing photographic hand tool 20 and which, as will be subsequently described, operates both independently of, as well as in communication with, various numerically controlled (or NC) processing and machining capabilities associated with the machine, farther such that the digitizing tool 20 can be remotely positioned in an external joint environment (such as for use within the patient body cavity, or in situ positioned, for scanning worn or fractured joints or bones) and for effectuating replacement of a damaged subset portion of an existing natural or synthetic joint assembly.

Figure 4:
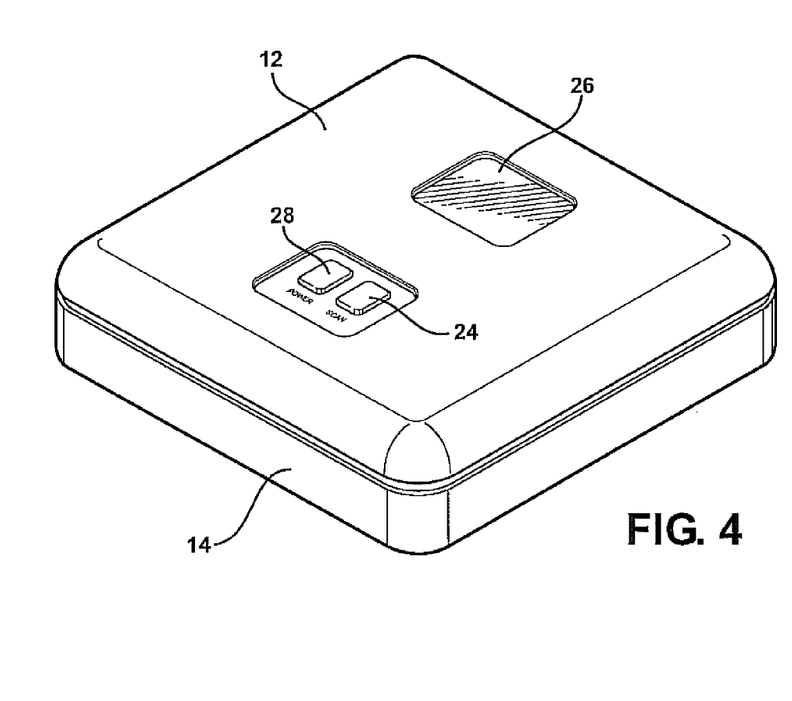
FIG. 4 is a sectional illustration of the uppermost located scanner compartment incorporating power and scan buttons, as well as scan window.

Referencing again FIGS. 1,2 and 4, the upper level scanner 12 includes such as a power button 22, scan button 24 and scan window 26. As with each of the stackable components 12-18, the scanner 12 exhibits a generally polygonal (four sided square) shape having a selected thickness. The scan window 26, according to one variant, can be opened (not shown), such as in order to reveal an interior volume associated with the upper level scanner 12, this further being of sufficient dimension to permit placement therein of a smaller sized implants or cartilage portions for replication.

The surface positioned scan window 26 is further understood to function in one embodiment to digitize and generate a substantially two dimensional profile of a desired implant to be produced. It is further understood that the interior of the scanner compartment 12 can additionally provide base, side and top scan surfaces (or mirrors), these farther capable of being positioned or arrayed within an interior of the scanner compartment 12 in such as fashion as to facilitate the generation of highly detailed and anatomically correct data for subsequently creating a three dimensional digitized copy/representation of a desired implant to be produce. Such implants (not shown) are understood to include any of an existing part removed from the patient for replication, as well as a cast or other low grade two or three dimensional model or template for providing the necessary dimensions for subsequent replication.

The scanner unit 12 is further understood to incorporate known digitizing technology, the use and manipulation of which is understood to be within the skill of one of ordinary skill in the art, and which enables it to produce a detailed three dimensional map of the implant configuration which is desired to be copied for subsequent interfacing with the carousel 14 and CNC machining 16 components. As will also be described in reference to the remote and multi-functional hand tool 20, the scanner 12 may include a wireless receiver which operates in a second application to receive a (wireless) transmitted signal from the hand tool, this being alternatively communicated to the additional operating components of the machine. Other variants also include a dedicated communication line (not shown) being established between tire hand tool and the digitizing interfacing component (e.g. processor) associated with the scanner 12 compartment.

Figure 5:
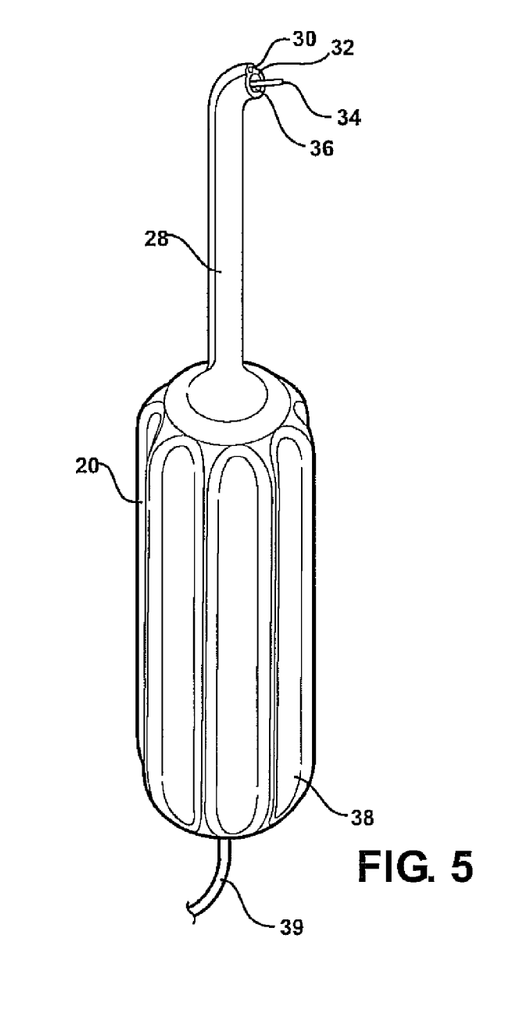
FIG. 5 is an illustration of a multi-functional remote combination laser machining and digitizing photographic hand tool, this operating within a joint environment and in communication and cooperation with processing capabilities built into the machining enclosure, such as for effectuating replacement of a damaged subset portion of an existing natural or synthetic joint assembly.

Referring again to FIGS. 1-3 and 5, the remote combination machining laser and digitizing photographic hand tool 20 is illustrated operating within a joint environment and in communication and cooperation with processing capabilities built into the machining enclosure, such as again for effectuating replacement of a damaged subset portion of an existing natural or synthetic joint assembly. As best shown in FIG. 5, the hand tool 20 exhibits a gripping handle from which extends a stem 28 terminating in a multi-functioning upturned end.

Features built into the tool 20 include such as an illuminating (such as fiber optic/LED or the like) light source 30, a combination digital camera/scanner unit 32 (this provided such as for taking a 3D digital photo of an area existing inside a joint and such as associated with a laser machined and sectioned location for which a desired implant portion is desired to be produced), a laser cutter 34, and a proximately located vacuum orifice 36 which withdraws and communicates shavings and the like to a based located collection bin 38 defined within the hand tool handle (and such as which can be emptied via a slide open door or accessible screw end cap (not shown). Although not shown, additional internal features associated with the hand tool can include such as a battery power source for operating the various described components.

A digital wireless transmitter is also incorporated into the tool 20 (extending from such as a handle end location at 39 in FIG. 5) and in order to transmit digitized data taken by the camera/scanner to the scanner unit 12 associated with the body of the machine 10. As previously described, appropriate digitization technology is known in the relevant art and can be adapted for incorporation into the hand held tool 20, in similar fashion to such technology concurrently being incorporated into the electronic architecture of the scanner compartment 12. It is again understood that, although not shown, a wired variant can again substitute for the wireless antenna 39 and can hardwire connect the remote tool 20 directly with an input location associated with the scanner.

In this fashion, and as will be further described in reference to future described embodiments, the inserting tip of the hand tool 20 is capable of operating within a remote human or other animal joint environment, such as during scanning/cutting/vacuuming steps, and in order to prepare the interior joint environment for the subsequent manufacture and installation of a desired and high tolerance matching cartilage portion or smaller sized implant replacement, such again further being facilitated by wireless communication of 3D digital data from the tool 20 to the scanner unit 12 as an alternate to directly placing a 3D article to be replicated within he scanner compartment 26. A remote tool storage receptacle 40 is also configured, such as along an exterior surface of the main machining component 16 (see again FIG. 1), for receiving and supporting the hand tool 20 in a secure and accessible location when such is not in use.

Figure 6:
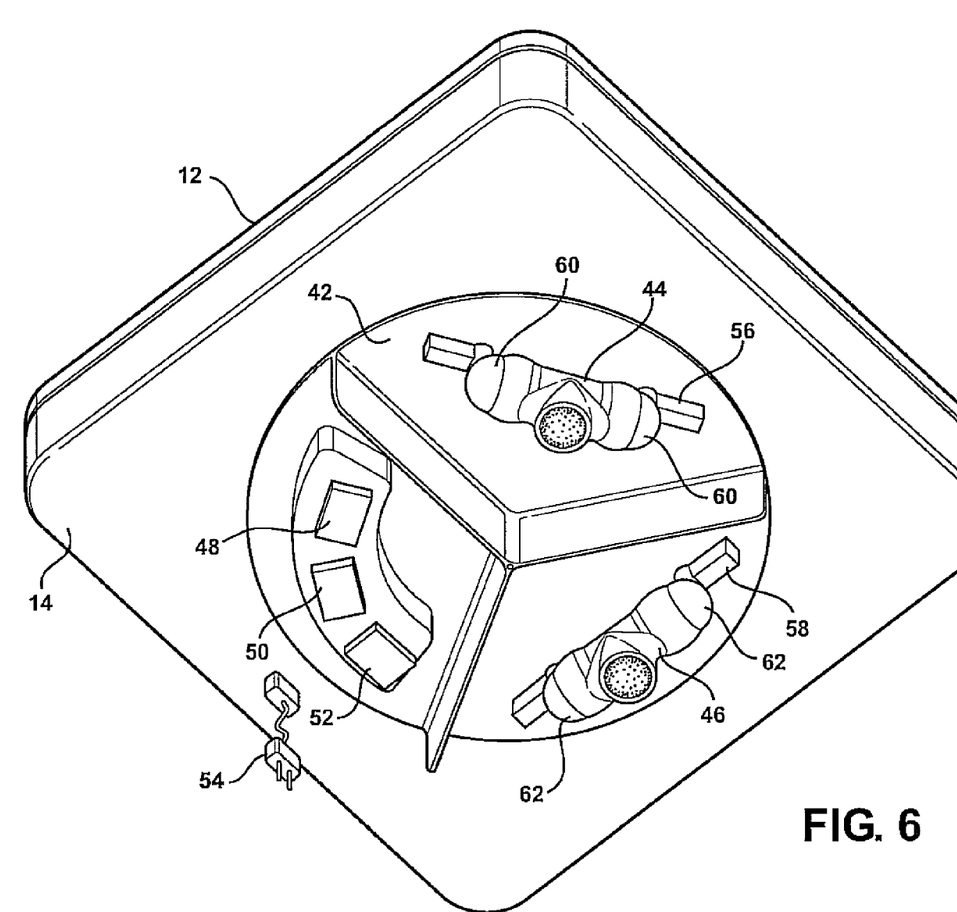
FIG. 6 is an underside perspective of the rotating carousel, also shown in FIG. 3, and enlarged to further illustrate individual small and large sized implant blanks as well as varying sized cartilage implants for selectively positioning within an interior defined machining environment.

Referring now to FIGS. 2 and 6, the underside positioned carousel 14 is again shown (a rear side of the carousel being integrally attached in downwardly facing fashion to the scanner 12) and exhibits a rotating circular platform 42 upon which are secured (in likewise downwardly facing fashion) a plurality of three individual compartments, these respectively including a first smaller sized implant blank 44, a second larger 46 sized implant blank, and a third individual plurality of cartilage blanks 48, 50 and 52. Also shown in FIG. 6 is an electrical connection 54, such as is used for engaging a socket location within the CNC compartment 16 and in order to provide power to rotate the carousel. Also shown in regards to the implant blank compartments are support rails 56 and 58, upon which are secured pairs 60 and 62 of linearly actuating and opposing end supports, these being either spring loaded or otherwise inwardly biasing for securing the implant blanks 44 and 46 thereupon and therebetween.

Figure 7:
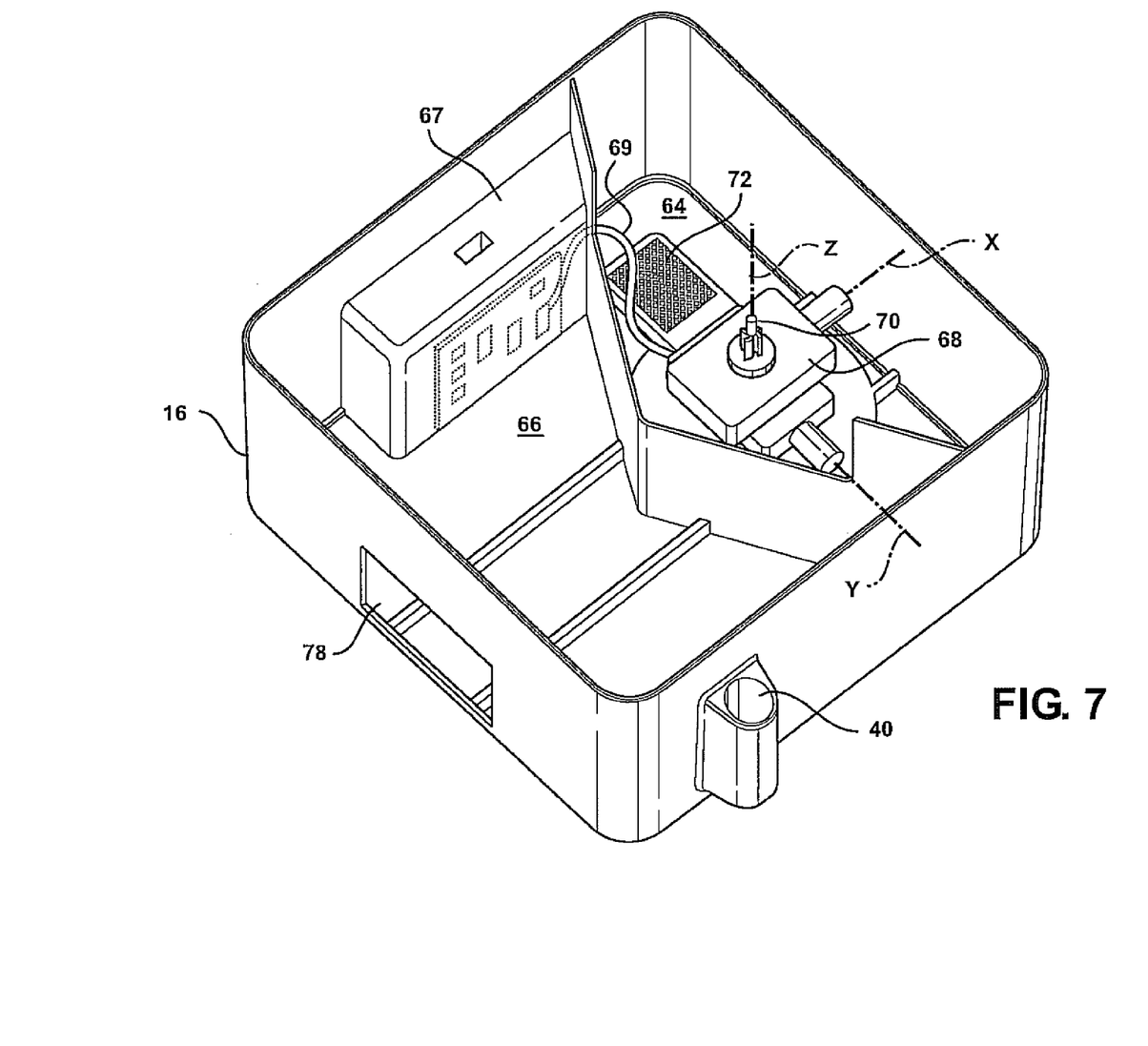
FIG. 7 is an enlarged perspective of the inner CNC machining component, this operating in communication with, the overhead and underside positioned rotatable carousel for machining a selected implant or cartilage, combined with, a removal drawer within which a finished implant/cartilage is deposited by the carousel.

FIG. 7 illustrates an enlarged perspective of the inner CNC machining component 16, this constituting a generally third level of the portable machining assembly and operating in communication with the overhead secured and underside communicable rotatable carousel 42 for successively positioning and then machining a selected implant 44 or 46 or cartilage 48, 50, or 52. As also illustrated in FIG. 2, the CNC machining component 16 exhibits a substantially open interior which is subdivided into a first machining zone 64 and a second finished tool deposit zone 66.

A portable 3D CNC cutting machine subassembly is generally represented at 68, this being traversable along each of X, Y and Z axes as is shown in FIG. 7. The technology surrounding the CNC subassembly 68 need not be further described beyond stating that appropriate known and conventional machining technology is capable of being integrated into the present machine and communicated by appropriate microprocessor driven technology.

A tool cutting zone 64 is supported at an upward most extending location of the CNC cutting machine subassembly 68 and is responsive to numerical input controls, this such as associated with the further processor subassembly either built into the machine, see for example as shown in phantom located within compartment 67 and which connects to cutting zone 64 via communication line 69 in order to instruct a machining protocol for a replacement article to be produced from one of die blanks. Alternatively, the required processor input can be inputted via an external PC or hard drive (not shown) in order to continually position and reposition die upwardly extending cutting tool 70 relative to a carousel platen 42 rotated and repositioned implant or cartilage blank. An associated tool bit is selected for mounting within an upwardly directed spindle assembly associated with the cutting zone, as again shown at 70, and is preferably rated for machining hard/soft synthetic plastics typically associated with such implants or cartilages.

A pair of ports are shown at 72 and 74 (see again FIGS. 3 and 7) and are powered by a portable vacuum built into an underlying and communicating fourth level vacuum box 18. The vacuum ports 72 and 74 operate to remove dust and smaller sized shaving particles from machining process, following the completion of which the carousel platen 42 is rotated with the finished machined implant or cartridge for releasing (via controls built into each pair of linear actuating end supports 60 or 62, or other suitable release mechanism associated with the individual cartilage blanks 48, 50 and 52) the finished machined product into the tool deposit zone 66.

A drawer 76 is mounted within an opening 78 (see FIG. 7) communicable with the tool deposit zone 66 and such that, upon completion and depositing of the finished item, the drawer 76 can be automatically opened (such as by internal controls) for releasing the product for removal from the machine. It is also envisioned that, depending upon the embodiment, the drawer may not include a configured handle, and such as for preventing access to the machine interior until completion of the machining cycle. That said, additional variants can contemplate the provision of a handle configured pull drawer, and which can further be locked until completion of the machining and depositing cycles.

Figure 8:
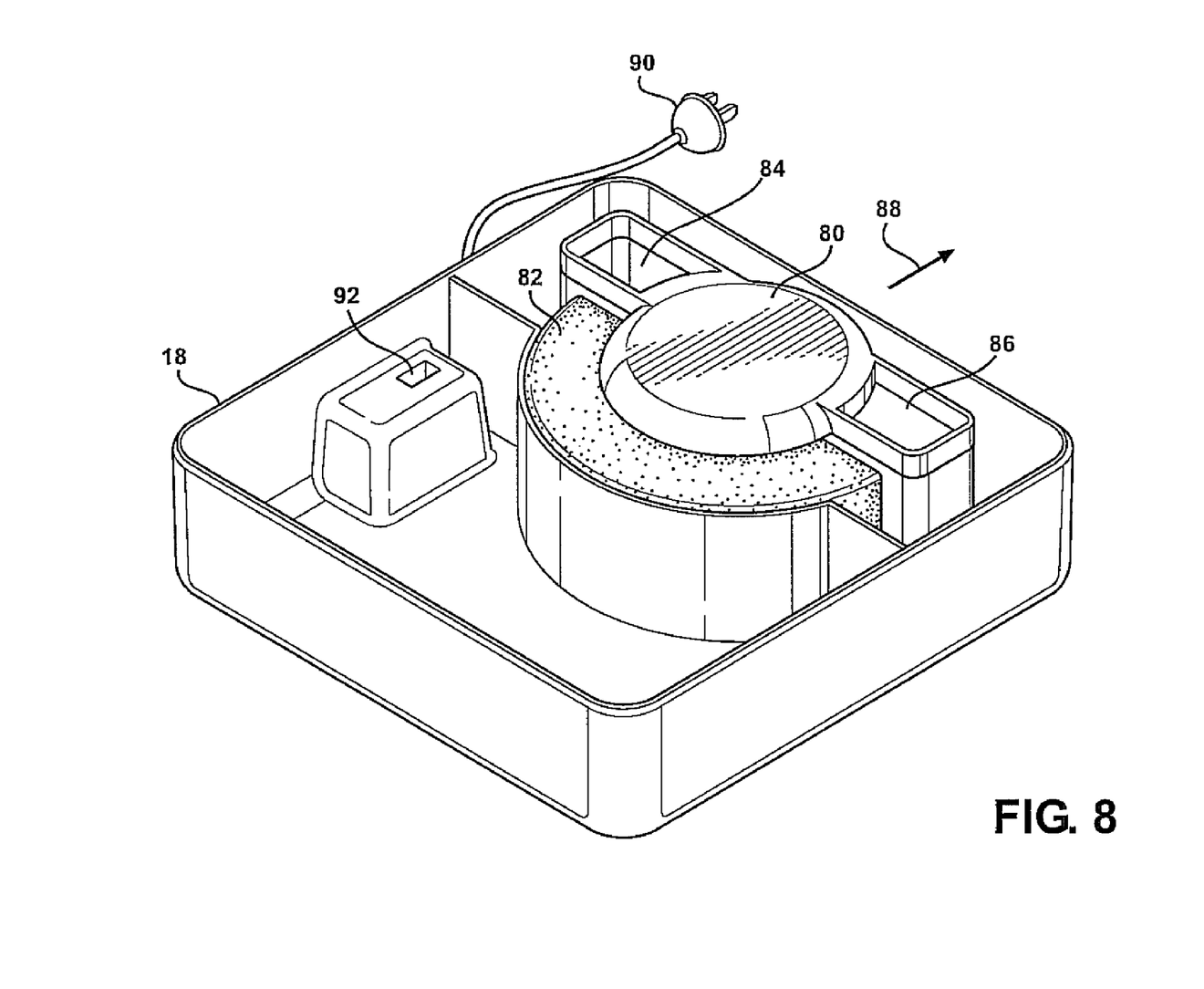
FIG. 8 is an enlarged perspective of a lowermost positioned vacuum collection box for collecting machining shavings, such as through communicating vacuum ports formed in the bottom side of the machining component, and for depositing into a shrapnel bin for subsequent removal.

Referring to FIG. 8, an enlarged perspective is shown of the lowermost positioned vacuum collection box 18, again for collecting machining shavings resulting from the CNC machining process described in reference to FIG. 7. An electrical powered vacuum is shown at 80, and around which is configured a filter 82. The vacuum communicates with the underside defined ports 72 and 74 of the CNC machining compartment 16, via shrapnel/chip/dust collection bins 84 and 86 defined within the mating locations in the vacuum box into which are deposited the waste items associated with the machining process for subsequent removal. The path of the exhaust follows arrow 88, this corresponding with a vent (not shown) defined along a rear surface of the vacuum box 18.

Also shown in FIG. 8 is the provision of a power cord 90 for powering die vacuum motor 80, as well as the CNC machining functions, the rotatable platen 42 and the upper disposed scanner. A socket 92 is also shown in FIG. 8, and to which the electrical connection socket 54 (previously shown in FIG. 3 in relation to the underside facing carousel 14) can be engaged for powering the upper component layers of the assembly. Although not specifically detailed, it is understood that any appropriate wiring scheme can be employed into the machine for communicating power from such as the lower most level, associated with the power cord 90, to the various interrelating and functioning components.

Figure 9:
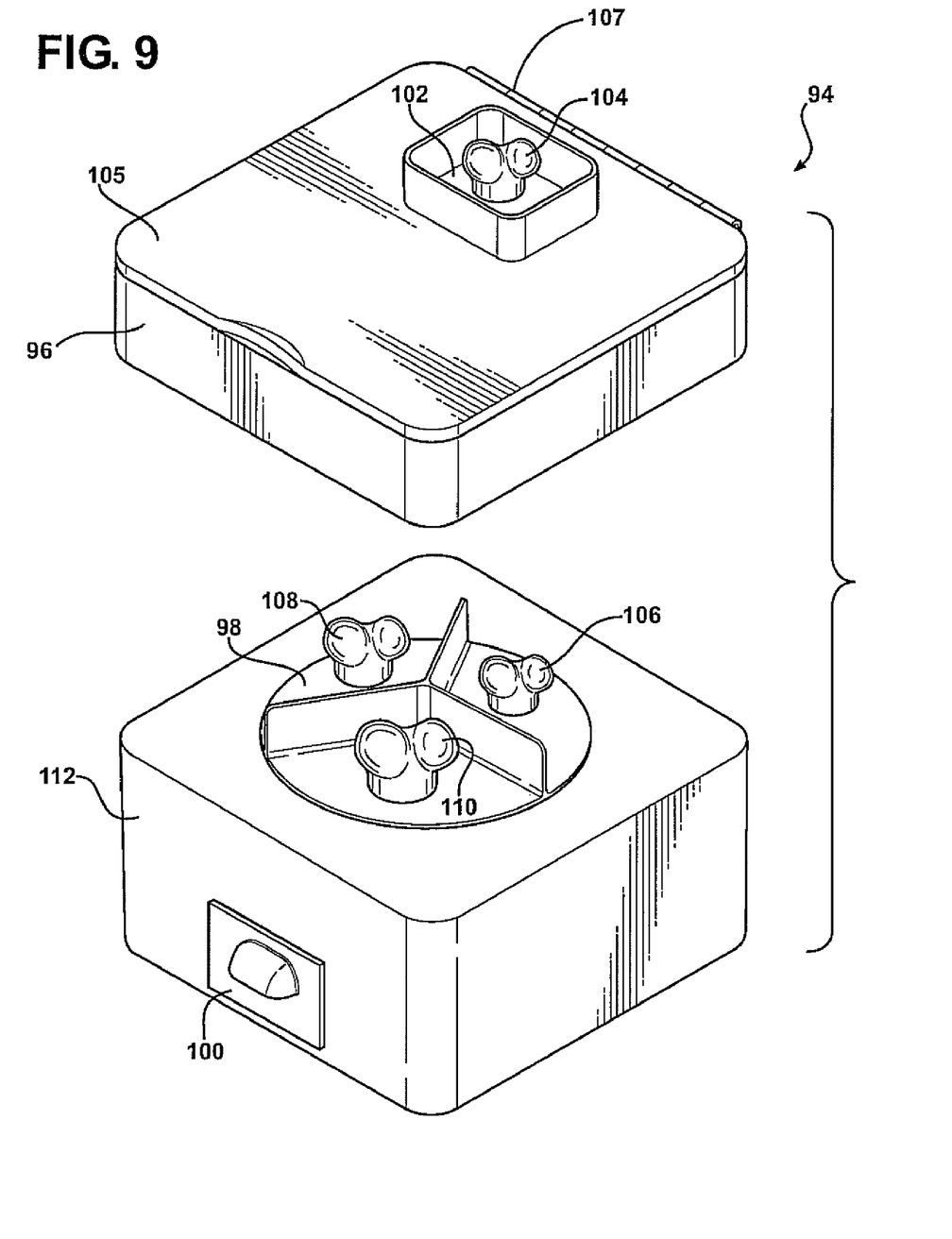
FIG. 9 is an exploded illustration of a portable joint implant manufacturing device according to a further preferred embodiment, and including a flatbed digital scanning component built into the scanner assembly in overhead communication with an upper side disposed three position carousel and lower disposed finished implant retrieval drawer.

Having now undertaken a detailed explanation of the CNC operable and joint/cartilage producing machine 10, reference will now be made as to a number of joint implant and cartilage applications which are made possible by the machining processes described herein. FIG. 9 is an exploded illustration of a portable joint implant manufacturing device 94 according to a further preferred embodiment and including a flatbed digital scanning component 96 built into the scanner assembly in overhead communication with an upper side disposed three position carousel 98 and lower disposed finished implant retrieval drawer 100.

The assembly of FIG. 9 consists of an alternate configuration, as opposed to that detailed throughout FIGS. 1-8, and of a scanning, repositioning, machining and depositing assembly for producing a precise 2D sectioned bone mounted end associated with a replacement implant or cartilage. Of note, a flatbed scanner 102 is associated with the upper positioned component 96 and into which is placed a selected implant item 104 for which replication by a new replacement implant is desired.

In the particular configuration shown in FIG. 9, the flatbed scanner 102 is configured in this particular environment for providing detailed 2D measurement of section bone end mounting cross section, this in order to precisely machine the inner and outer annular dimensions associated with the bone mounting surface of the implant and in order to guarantee a precise fit when mounted within the joint environment. AM 105 is provided, and upon which the surface located scanner 102 is positioned. The lid 105 can be pivoted, via hinges 107, to an open position and to reveal an interior of the scanning compartment 96, and such as which can contain further scanning facilities for creating larger 2D or 3D digitized models of a sample template implant or cartilage in similar fashion as previously described.

As further shown in reference to the carousel 98, three positions are again shown for segregating small 106, medium 108 and large 110 sized implants, these being mounted in downwardly facing manner (and again, so that the sectioned bone end mounting locations project in underside communicating fashion with an interior of an underlying machine zone 112 associated with the alternate variant of FIG. 9. Following scanning at the first upper level of the previous item 104 to be replicated, the carousel platen 98 is rotated so that a desired sized replacement implant is repositioned with its downwardly extending bone end mounting profile (not shown) projecting in downward and communicating fashion with an interior location of the machining zone cavity 112, and within which is mounted the suitable CNC machining sub-assembly (also not shown but understood to correspond to that previously described). Following the NC controlled machining process (see again previous description associated with FIG. 7 and which contemplates machining while the implant is supported upon the platen carousel), this finished implant article is rotated and deposited for removal via the drawer 100.

Figure 10:
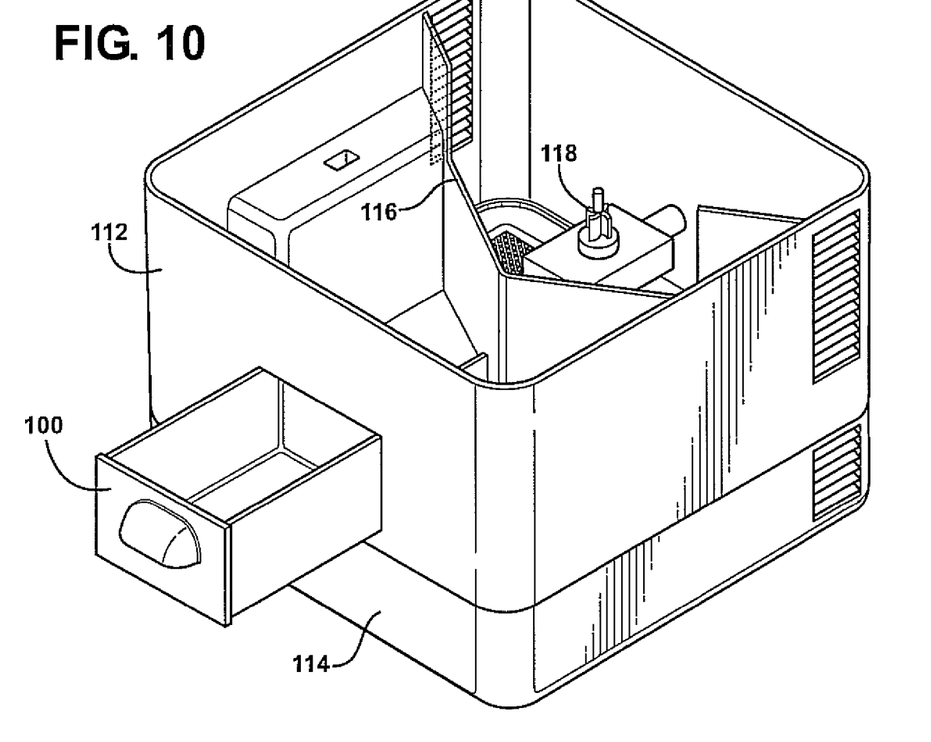
FIG. 10 is an illustration of both a third level CNC machining zone and a fourth level waste deposit and retrieval enclosure associated with the portable implant device of FIG. 9.

FIG. 10 is an illustration of both an interior cutaway of a third level CNC machining zone, again shown at 112, and a fourth level waste deposit and retrieval enclosure 114, associated with the portable implant device of FIG. 9. As with the first disclosed variant, the CNC machining zone includes an inner partition 116 for separating the CNC cutting zone 118 from the remainder of the cavity interior. A 2D machining process is performed by the associated cutting tool, this providing a machined profile matching the 2D scanned data regarding the desired sectioning bone end mounting data. Consistent with earlier variants, the machined dust and waste shavings from die implant machining operation is vacuum withdrawn into the lower collection enclosure 114 for later removal.

Figure 11:
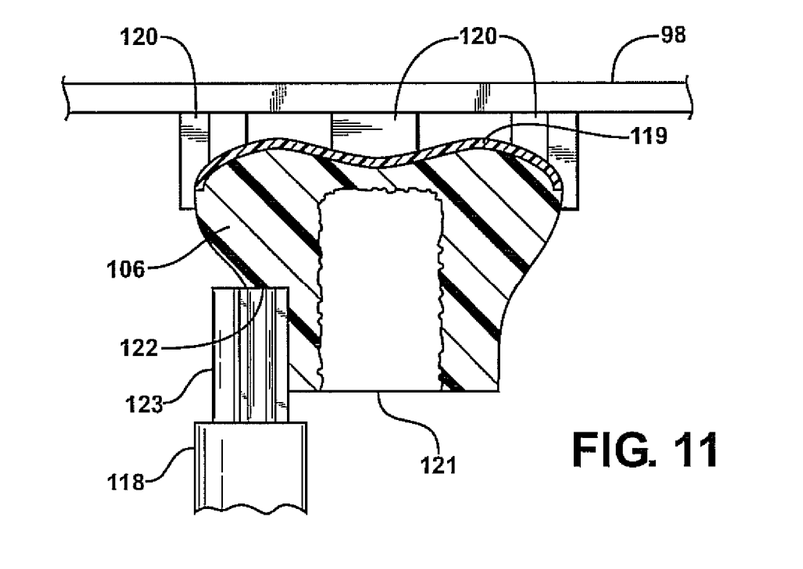
FIG. 11 is an illustration of CNC machining being performed on a carousel supported implant.

As is now shown in FIG. 11, a more detailed sectional illustration is provided of a CNC machining operation being performed on a selected carousel supported implant (e.g. as previously shown at 106 in FIG. 9). As described previously, a top cartilage 119 surface of the joint is secured, in this version via suction or other suitable adhering locations or the like (see at 120) and which project downwardly from the rotatable turntable 98, for preventing movement of an underside bone mounting perimeter 121 associated with the implant 106, during machining by the 2D cutter, see at 123. As is also shown, a unique stepped configuration is imparted in the bone end mounting perimeter 121 (see further inward step 122) this facilitating a more precise fit when secured to the sectioned bone end (not shown) associated with the patient.

Figure 12:
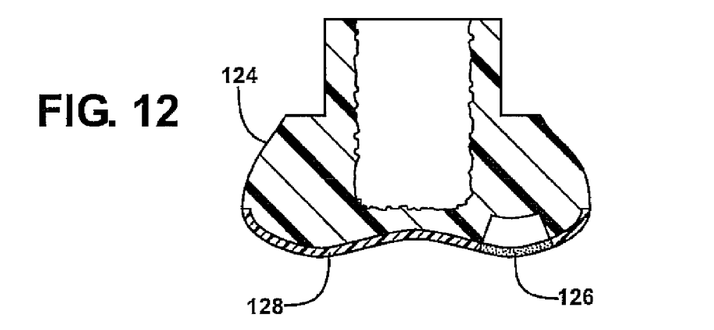
FIG. 12 is a cutaway illustration of an existing implant with cutout section, such as sectioned by the remote tool associated with the present invention.

FIG. 12 is a cutaway illustration 124 of an existing (e.g. typically composite hard plastic) implant with cutout section 126, this in turn being defined within soft plastic cartilage layer 128. The cutout section 126 is, according to one preferred embodiment, removed by such as the remote tool (see previously as described at 20 in FIG. 5).

Figures 12A, 13:
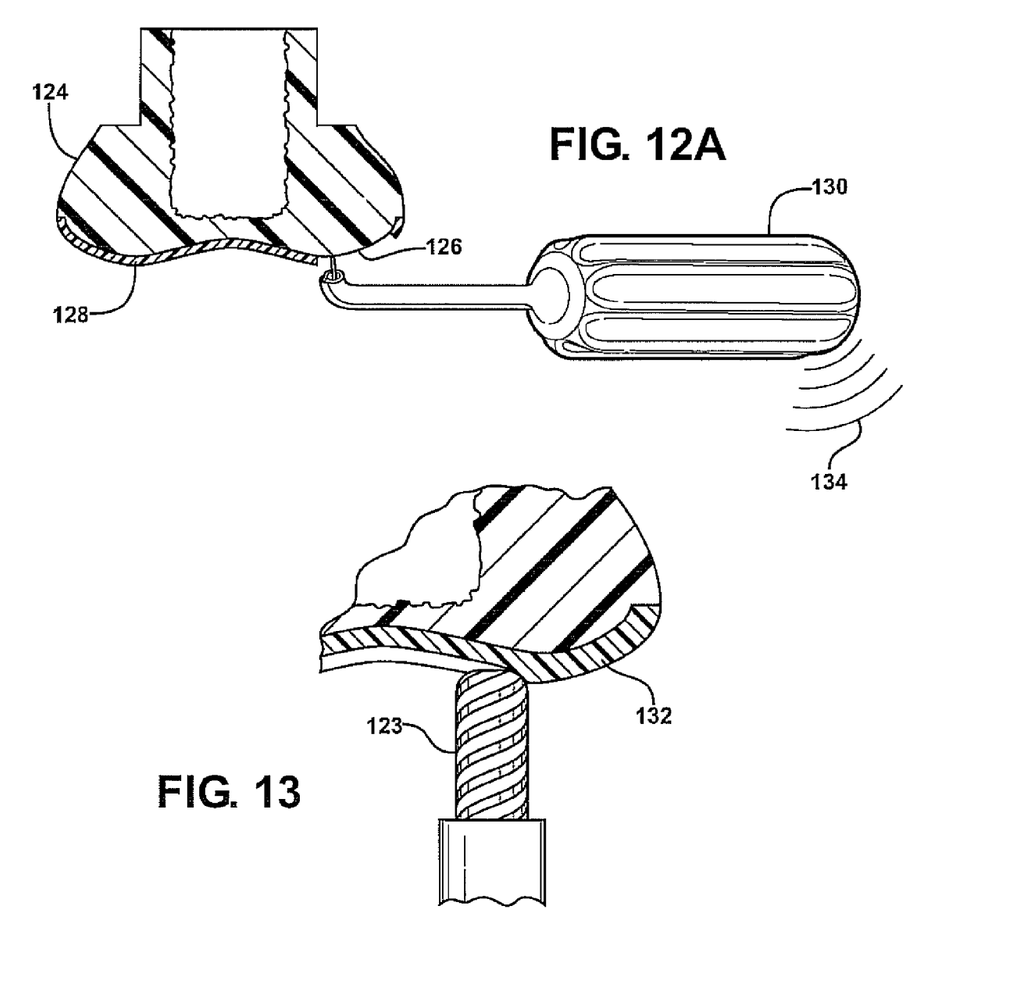
FIG. 12A is a succeeding illustration of a remote and multi-functional hand tool employed in a first scanning configuration to transmit dimensioning information to a remote machining station, such as associated with a cartilage replacement for the artificial implant cut-out section.
FIG. 13 is a sectional view of a machining step undertaken by the CNC cutter upon a cartilage implant blank and according to the digitized signal transmitted by the hand tool.

FIG. 12A is a succeeding illustration of a remote and multi-functional hand tool 130, this employed in a first scanning configuration to transmit dimensioning information to a remote scanner input location associated with a machining station, and such as further associated with a desired cartilage replacement for installing within the artificial implant cut-out section. It is also contemplated that the tool 130 can be employed (in much the same fashion as described in reference to the tool 20 in FIG. 1) in a first operation to section/clean a joint or cartilage area to be replicated (see again operation of FIG. 12A) following which the tool 130 is re-employed in a digitized scanning function to transmit the necessary information for subsequent replication of the necessary replacement article.

Finally, and referring to FIG. 13, a sectional view is shown of a machining step undertaken by the CNC cutter 123 previously described, and such as upon a cartilage implant blank 132 constructed of a soft plastic material, this according to the digitized signal transmitted by the hand tool 130 and generally referenced at 134. The cartilage blank 132 is mounted in a similar fashion as described in reference to the implants 106-110, and reference is again made to the initial embodiment described in FIGS. 1-8.

Having described my invention, other and additional preferred embodiments will become apparent to those skilled in the art to which it pertains, and without deviating from the scope of the appended claims.

The invention claimed is:

1. A machine for producing a three dimensional joint replacement article, comprising:
a three dimensional shaped body incorporating a scanner component for at least receiving a digitized input corresponding to a set of dimensions associated with a three dimensional joint replacement article to be produced;
a carousel mounted within said body and supporting thereon a plurality of material blanks, each blank corresponding to a three dimensional joint replacement article to be produced;
said body further comprising a numerical control guided machining subassembly situated within said body in machining communication with at least one of said material blanks mounted on said carousel, said machining subassembly being located beneath said carousel; and
a retrieval location associated with said body and into which a machined one of the blanks in the form of a finished part is deposited following conclusion of machining.

2. The machine as described in claim 1, said scanner component further comprising a scan window defining access to an interior compartment of the body for receiving an existing article to be measured for replication.

3. The machine as described in claim 1, wherein said plurality of material blanks supported on said carousel correspond to at least one of implant and cartilage replacement articles, said carousel being selectively actuated to position a selected one of the blanks in machining communication with said machining subassembly.

4. The machine as described in claim 3, wherein said carousel is mounted with said scanner component in a position that is under the scanner component and that is above an open interior compartment associated with said numerical controlled machining subassembly, said carousel further comprising adjustable and actuatable mounting assemblies for securing said implant and cartilage blanks for machining and for successive depositing of the respective finished parts into a drawer associated with said retrieval location.

5. The machine as described in claim 4, said retrieval drawer being secured within a finished part repository incorporated into said open interior compartment and separated from the machining subassembly by an inner partition.

6. The machine as described in claim 3, further comprising a waste removal enclosure positioned underneath said machining subassembly and incorporating a vacuum interconnected with said machining subassembly via at least one vacuum port in order to remove machined waste resulting from a numerical controlled operation performed by said machining subassembly on one of the material blanks.

7. The machine as described in claim 6, further comprising a power cord communicating with said waste removal enclosure for powering said vacuum, said numerical controlled machining subassembly, said carousel and said scanner component.

8. The machine as described in claim 7, further comprising a processor communicable with said machining subassembly for dictating a machining protocol associated with an article to be produced.

9. The machine as described in claim 1, further comprising a remote hand-held tool interfacing with said scanner component and comprising a 3D digitizing camera and scanner and at least one of a wired or wireless connection to said scanner component for effectuating digitizing of at least one of a two dimensional and a three dimensional image associated with an article to be replicated.

10. The machine as described in claim 9, said hand tool further comprising a stem interconnecting with a handle and exhibiting at least one of a machining laser, a portable vacuum communicating to a handle reservoir, and a light emitting source.

11. A machine for producing a three dimensional joint replacement article, comprising:
a body establishing an interior enclosure separated into multiple layers and including an uppermost layer incorporating a scanner component for receiving a digitized input corresponding to a set of dimensions associated with a three dimensional joint replacement article to be produced, said scanner component further comprising a scan window defining access to an interior compartment for receiving an existing article to be measured for replication;
a carousel mounted within said body and supporting thereupon a plurality of material blanks corresponding to at least one of implant and cartilage replacement articles, said carousel being selectively actuated to position a selected blank mounted thereon in machining communication with a numerical controlled machining subassembly located underneath said carousel; and
a retrieval location associated with said body and into which a finished part fashioned from the selected blank is deposited following conclusion of machining of the selected blank.

12. The machine as described in claim 11, wherein said carousel is mounted with said scanner component in a position that is under the scanner component and that is above an open interior compartment associated with said numerical controlled machining subassembly, said carousel further comprising adjustable and actuatable mounting assemblies for securing said implant and cartilage blanks for machining and for successive depositing of the respective finished parts into a drawer associated with said retrieval location.

13. The machine as described in claim 12, said retrieval drawer being secured within a finished part repository incorporated into said open interior compartment and separated from the machining subassembly by an inner partition.

14. The machine as described in claim 11, further comprising a waste removal enclosure positioned underneath said machining subassembly and incorporating a vacuum interconnected with said machining subassembly via at least one vacuum port in order to remove machined waste resulting from a numerical controlled operation performed by said machining subassembly on one of the material blanks.

15. The machine as described in claim 14, further comprising a power cord communicating with said waste removal enclosure for powering said vacuum, said numerical controlled machining subassembly, said carousel and said scanner component.

16. The machine as described in claim 15, further comprising a processor built into said interior enclosure and communicable with said machining subassembly for dictating a machining protocol associated with an article to be produced.

17. The machine as described in claim 11, further comprising a remote hand-held tool interfacing with said scanner component and comprising a 3D digitizing camera and scanner and at least one of a wired or wireless connection to said scanner component for effectuating digitizing of at least one of a two dimensional and a three dimensional image associated with the existing article to be replicated.

18. The machine as described in claim 17, said hand tool further comprising a stem interconnecting with a handle and exhibiting at least one of a machining laser, a portable vacuum communicating to a handle reservoir, and a light emitting source.

19. A machine for producing a three dimensional joint replacement article, comprising:
- a three dimensional shaped body for receiving a digitized input corresponding to a set of dimensions associated with a three dimensional joint replacement article to be produced;
- a remote hand-held tool interfacing with said body and comprising a 3D digitizing camera and scanner and at least one of a wired or wireless connection to the body for effectuating digitizing of at least one of a two dimensional and a three dimensional image associated with an article to be replicated;
- a carousel mounted within said body and supporting thereon a plurality of material blanks, each blank corresponding to a three dimensional joint replacement article to be produced;
- said body further comprising a numerical control guided machining subassembly situated within said body in machining communication with at least one of said material blanks mounted on said carousel, said machining subassembly being located beneath said carousel; and
- a retrieval location associated with said body and into which a machined one of the blanks in the form of a finished part is deposited following conclusion of machining.

20. The machine as described in claim 19, said hand tool further comprising a stem interconnecting with a handle and exhibiting at least one of a machining laser, a portable vacuum communicating to a handle reservoir, and a light emitting source.

* * * * *

UNITED STATES PATENT AND TRADEMARK OFFICE
CERTIFICATE OF CORRECTION

PATENT NO. : 8,327,519 B2  Page 1 of 1
APPLICATION NO. : 12/422412
DATED : December 11, 2012
INVENTOR(S) : Linares It is certified that error appears in the above-identified patent and that said Letters Patent is hereby corrected as shown below:

On the title page item [57] line 6, Delete "die", Insert -- the --

Signed and Sealed this
Nineteenth Day of May, 2015

Michelle K. Lee
*Director of the United States Patent and Trademark Office*